United States Patent
Destaillats et al.

(10) Patent No.: US 9,000,039 B2
(45) Date of Patent: Apr. 7, 2015

(54) SN-1(3) MONOACYLGLYCERIDES AND LIPID ABSORPTION

(75) Inventors: Frederic Destaillats, Servion (CH); Cristina Cruz-Hernandez, Epalinges (CH); Fabiola Dionisi, Epalinges (CH); Isabelle Masserey-Elmelegy, Epalinges (CH); Manuel Oliveira, Chexbres (CH); Julie Moulin, Attalens (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 14/009,981

(22) PCT Filed: Apr. 3, 2012

(86) PCT No.: PCT/EP2012/056080
§ 371 (c)(1),
(2), (4) Date: Oct. 4, 2013

(87) PCT Pub. No.: WO2012/136659
PCT Pub. Date: Oct. 11, 2012

(65) Prior Publication Data
US 2014/0031426 A1    Jan. 30, 2014

(30) Foreign Application Priority Data
Apr. 4, 2011 (EP) .................... 11160929

(51) Int. Cl.
| | | |
|---|---|---|
| *A61K 31/22* | (2006.01) | |
| *A23L 1/30* | (2006.01) | |
| *A61K 31/23* | (2006.01) | |
| *A61K 31/231* | (2006.01) | |
| *A61K 31/232* | (2006.01) | |
| *A61K 31/25* | (2006.01) | |
| *A61K 45/06* | (2006.01) | |

(52) U.S. Cl.
CPC ............ *A61K 31/232* (2013.01); *A23L 1/3008* (2013.01); *A61K 31/23* (2013.01); *A61K 31/231* (2013.01); *A61K 31/25* (2013.01); *A61K 45/06* (2013.01)

(58) Field of Classification Search
USPC ........................................... 514/549
See application file for complete search history.

(56) References Cited

U.S. PATENT DOCUMENTS

| | | | |
|---|---|---|---|
| 2004/0204486 A1 | 10/2004 | Hogestatt et al. | |
| 2009/0023807 A1* | 1/2009 | Harbige et al. | 514/549 |
| 2009/0292019 A1* | 11/2009 | Fortin | 514/549 |
| 2010/0249080 A1* | 9/2010 | Burry et al. | 514/162 |
| 2013/0109753 A1* | 5/2013 | Bistrian et al. | 514/560 |

FOREIGN PATENT DOCUMENTS

| | | |
|---|---|---|
| DE | 2935546 | 3/1981 |
| EP | 1864657 | 12/2007 |
| JP | 2010132631 | 6/2010 |
| WO | 2010149170 | 12/2010 |
| WO | 2011029099 | 3/2011 |
| WO | 2011092299 | 8/2011 |

OTHER PUBLICATIONS

Harbige et al. CAS: 145: 306838, 2006.*
Shin et al. CAS: 148: 529469, 2008.*
Fortin's CAS: 152: 1819, 2009.*
Haneda et al. CAS: 153:97755, 2010.*
Li et al. CAS: 155:143114, 2010.*
Banno et al. "Lymphatic Absorption of Docosahexaenoic Acid Given as Monoglyceride, Diglyceride, Triglyceride, and Ethyl Ester in Rats" J Nutr Sci Vitaminol, vol. 48, 2002, pp. 30-35, XP002395871.
Chang et al. "Monoglycerides from the brown alga *Sargassum sagamianum*: Isolation, synthesis, and biological activity" Bioorganic & Medicinal Chemistry Letters, vol. 18, 2008, pp. 3589-3592, XP002649776.

* cited by examiner

*Primary Examiner* — Rei-tsang Shiao
(74) *Attorney, Agent, or Firm* — K&L Gates LLP

(57) ABSTRACT

The present invention relates generally to the field of lipids and in particular aims at improving lipid absorption, for example under conditions of lipid maldigestion or malabsorption. One embodiment of the present invention relates to a composition comprising sn-1(3) monoacylglycerols, wherein the sn-1 or sn-3 position is occupied by an acyl group such as a fatty acid and the sn-2 position remains unoccupied. The fatty acid may be one with anti-inflammatory properties.

15 Claims, 2 Drawing Sheets

Figure 1:
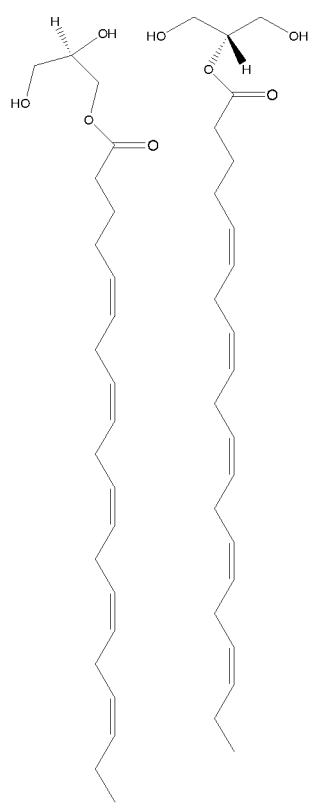

Figure 1: sn-1(3) monoeicosapentaenoylglycerol

SN-1(3) MONOACYLGLYCERIDES AND LIPID ABSORPTION

CROSS REFERENCE TO RELATED APPLICATIONS

The present application is a National Stage of International Application No. PCT/EP2012/056080, filed on Apr. 3, 2012, which claims priority to European Patent Application No. 11160929.3, filed Apr. 4, 2011, the entire contents of which are being incorporated herein by reference.

The present invention relates generally to the field of lipids and in particular aims at improving lipid absorption, for example under conditions of lipid maldigestion or malabsorption. One embodiment of the present invention relates to a composition comprising sn-1(3) monoacylglycerols, wherein the sn-1 or sn-3 position is occupied by an acyl group such as a fatty acid and the sn-2 position remains unoccupied. The fatty acid may be one with anti-inflammatory properties.

The delivery of bioactive fatty acids under conditions of malabsorption such as in pancreatic insufficiency, bile salt deficiency, and short gut due to gut removal or mucosal disease is critical.

In these physiological conditions, the digestion pathways, involving degradation of dietary triglycerides by the pancreatic lipase and the formation of micellar macrostructures required for enteral uptake, are impaired.

The delivery of bioactive fatty acids having, e.g., anti-inflammatory properties is therefore critical in these conditions as this type of fatty acids could help to lower the inflammation response.

Based on previously published prior art (Freeman CP, et al., J Dairy Sci 1965; 48:853-8; Innis S M, et al., Lipids 1994; 29:541-5) it is currently understood that fatty acids located in the sn-2 position of a glyceride are more readily absorbed by the body than fatty acids in the sn-1(3) position.

One would hence assume that the provision of monoacylglycerols (MAGs) with a fatty acid in sn-2 position would be an ideal vehicle to provide fatty acids that can be easily absorbed.

However, sn-2 MAGs are known to isomerise, for example, with storage times and/or elevated temperatures to yield a mixture of sn-1(3) and sn-2 MAGs (Compton D. L., et al., 20007; Lyubachevskaya G and Boyle-Roden E., 2000). Hence, the use of Sn-2 MAGs is presently not considered an option to provide fatty acids for absorption more effectively than using fish oil.

For humans, there is presently no dietary solution available to deliver essential fatty acids effectively, in particular when mechanisms involved in lipid digestion and absorption are impaired. Hence, in hospital generally parenteral nutrition formulations are used.

In aged companion animals, such as old dogs or cats for example, there is equally no solution available as well.

However, it would be desired to have a food composition available that allows the efficient uptake of fatty acids even under conditions of lipid malabsorption.

Hence, it was the object of the present invention to provide the art with an optimal glyceride structure allowing a substantial uptake of fatty acids, for example fatty acids with anti-inflammatory properties, such as EPA, in particular in malabsorption conditions. This glyceride structure should be more efficient in delivering fatty acids than fish oil.

The inventors were surprised to see that—contrary to what is currently assumed in the art—they could achieve this object by the subject matter of the independent claim. The dependent claims define further embodiments of the present invention.

The inventors found that they could significantly improve fatty acid absorption by using a mixture of sn-2 and sn-1(3) MAGs.

Remarkably, the mixture of sn-2 and sn-1(3) MAGs was found to more effective in delivering fatty acids for absorption than pure sn-2 MAGs, contrary to what is presently believed in the art.

In addition, the mixture of sn-2 and sn-1(3) MAGs was found to provide fatty acids even under maldigestion or malabsorption conditions more effectively than fish oil under normal conditions.

Hence, the present invention is related to the use of sn-1(3) MAGs, possibly in combination with sn-2 MAGs (see FIG. 1) to deliver bioactive fatty acids such as eicosapentaenoic acid (EPA), e.g., under lipid maldigestion or malabsorption conditions.

MAGs do not need to be digested prior to absorption and have intrinsic emulsifying properties allowing a good dispersion of oil droplets prior to absorption in the intestine.

The inventors tested their concept in a lipid maldigestion/malabsorption animal model. The malabsorption condition was obtained using Orlistat®, a well known pancreatic and gastric lipases inhibitor. Animals were fed with long-chain polyunsaturated fatty acid (LC-PUFA) supplements containing mainly eicosapentaenoic (EPA) acid. Fish oil was used as a source of triacylglycerols and different EPA glycerides, for example those of FIG. 1, were evaluated. At different time intervals the fatty acid profile of red blood cell and plasma lipids was assessed. At the end of the experiment, fatty acid profiles of different tissues were determined. A statistical evaluation revealed that the use of Orlistat® decreases EPA incorporation in red blood cells. The level of, e.g., EPA incorporated in red blood cells in an animal receiving the sn-1(3) MAGs of the present invention was found to be significantly higher compared to the administration of fish oil with mixture of EPA in sn-1, sn-2 and sn-3 positions. This clearly demonstrates that, e.g., in conditions of lipid malabsorption, the incorporation of LC-PUFA provided as triacylglycerols is reduced. However, if LC-PUFA are provided as sn-1(3) MAGs the incorporation in tissue is not altered in conditions of lipid malabsorption/maldigestion.

Hence, one embodiment of the present invention is a composition comprising an sn-1(3) MAGs.

The acyl group may be a functional fatty acid.

Functional fatty acids are for the purpose of the present invention fatty acids that deliver a health benefit.

For example, the functional fatty acid may be a fatty acid with anti-inflammatory properties. Which fatty acids have anti-inflammatory properties is known to those of skill in the art.

For example, fatty acids having anti-inflammatory properties may be selected from the group consisting of eicosapentaenoic acid (EPA), docosahexaenoic acid (DHA), α-linolenic acid (ALA), stearidonic acid (SA), γ-linolenic acid (GLA), dihomo-γ-linolenic acid (DGLA), docosapentanenoic acid (DPA), sciadonic acid and juniperonic acid.

Sciadonic acid is 5Z,11Z,14Z-eicosatrienoic acid. Juniperonic acid is 5(Z),11(Z),14(Z),17(Z)-eicosatetraenoic acid.

Typical MAGs that may be employed in the framework of the present invention may be selected from the group consisting of sn-1(3)-monoeicosapentaenoylglycerol, sn-1(3)-monodocosahexaenoylglycerol, sn-1(3)-monooctadecatrienoylglycerol, sn-1(3)-monooctadecatetraenoylglycerol, sn-1(3)-monoeicosatrienoylglycerol, sn-1(3)- monodocosapentaenoylglycerol, sn-1(3)-monosciadonylglycerol, sn-1(3)-monojuniperonylglycerol or combinations thereof.

Figure 2:
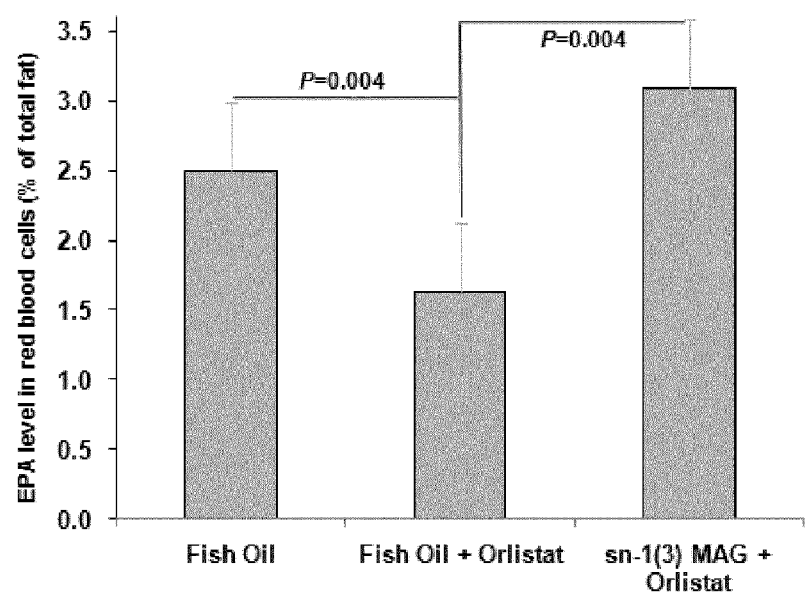

For example, the inventors obtained very good results with sn-1(3) monoeicosapentaenoylglycerol as sn-1(3)-monoacylglycerol. Here, even under maldigestion/malabsorption conditions the fatty acids were better absorbed that the fatty acids of fish oil under normal conditions (FIG. 2).

Of course, the composition may comprise a mixture of different MAGs with different fatty acids in the sn-1(3) position.

The fatty acids may be mixed in a way, for example, that a particular ratio between n-3 and n-6 fatty acids is used.

n-3 fatty acids include for example α-linolenic acid, stearidonic acid, eicosatrienoic acid, n-3 eicosatetraenoic acid, eicosapentaenoic acid, clupanodonic acid, docosahexaenoic acid, n-3 tetracosapentaenoic acid, or n-3 tetracosahexaenoic acid.

n-6 fatty acids include for example linoleic acid, γ-linolenic acid, n-6 eicosadienoic acid, dihomo-γ-linolenic acid, arachidonic acid, n-6 docosadienoic acid, adrenic acid, n-6 docosapentaenoic acid or calendic acid.

The composition may contain a combination of different sn-1(3) monoacylglycerides; for example with a ratio of n-3 to n-6 fatty acids of about 5:1 to about 15:1; for example about 8:1 to about 10:1.

For example, composition of the present invention may be for use in the delivery of fatty acids having anti-inflammatory properties.

The composition of the present invention is in particular useful under conditions of lipid maldigestion or malabsorption.

Consequently, the composition of the present invention may be to be administered to subjects suffering from a lipid maldigestion or malabsorption condition.

The composition is useful for subject suffering from any kind of lipid maldigestion or malabsorption condition. For example, such a malabsorption condition may be due to pancreatic insufficiency, bile salt deficiency, a mucosal disorder and/or a short gut.

For example, if the fatty acid comprised by the MAG derivative is a fatty acid having anti-inflammatory properties, the composition in accordance with the present invention may be for use in the treatment or prevention of inflammatory disorders.

The present invention also relates to the use of an sn-1(3) monoacylglycerol, wherein the acyl group is a fatty acid having anti-inflammatory properties for the preparation of a composition to treat or prevent inflammatory disorders, in particular under lipid maldigestion and/or malabsorption conditions.

The inflammatory disorder may be selected from the group consisting of acute inflammations such as sepsis, and chronic inflammations such as inflammatory bowel disease, Crohn's disease, ulcerative colitis, necrotizing enterocolitis, skin inflammation, such as UV or chemical-induced skin inflammation, eczema, reactive skin, psoriasis, vitiligo, acne, inflammatory bowel syndrome, liver inflammation, alcoholic cirrhosis, allergy, atopy, bone inflammation, rheumatoid arthritis, systemic lupus, dermato-myositis, thyroiditis, type I diabetes, celiac disease, Biermer's disease, multiple sclerosis, encephalomyelitis, eye inflammation, obesity-associated inflammation, age-related low-grade inflammation, Blau's syndrome, Alzheimer's disease, cardiovascular diseases, atherosclerosis, metabolic syndrome, or combinations thereof.

The composition of the present invention may comprise a mixture of sn-2 MAGs and sn-1(3) MAGs.

Depending on the nature of the fatty acid used as acyl-group in the sn-1(3) position such mixtures may form automatically through isomerisation.

Hence, the composition may comprise no more than 25 weight-%, preferably no more than 15 weight-% of the total MAGs as sn-2 MAGs.

Unwanted isomerisation may be prevented or at least slowed down significantly by adjusting the pH to the neutral range and/or by keeping the temperature of the composition low.

Hence, the composition may have a pH in the range of about 5-8, preferably about 5-7.

The composition may also be to be stored at 8° C. or below.

Isomerisation of the MAGs may further be prevented, even in the body after consumption by inhibiting the action of lipase B.

Hence, the composition may further comprise a lipase B inhibitor. Lipase B inhibitors are known to those of skill in the art. Edible lipase B inhibitors are preferred. "Edible" means that a material is approved for human or animal consumption.

The composition of the present invention may be any kind of edible composition. Preferably, the composition is a composition to be administered orally or enterally.

For example, the composition may be selected from the group consisting of a food product, an animal food product, a pharmaceutical composition, a nutritional composition, a nutraceutical, a drink, a food additive or a medicament.

For example, the composition may be a liquid nutritional formula to be administered enterally, e.g., in hospitals.

The composition may also be a nutritional formulation to be administered to people above the age of 60.

The composition may also be a powdered composition to be reconstituted in milk or water.

If the composition is provided in the form of a powder, it may be a shelf stable powder. Shelf stability can be obtained, for example by providing the composition with a water activity smaller than 0.2, for example in the range of 0.19-0.05, preferably smaller than 0.15. Water activity or $a_w$ is a measurement of the energy status of the water in a system. It is defined as the vapor pressure of water divided by that of pure water at the same temperature; therefore, pure distilled water has a water activity of exactly one.

The caloric density of the composition of the present invention may be adjusted to the needs of the patient.

For example, the composition in accordance with the present invention may have a caloric density in the range of 0.5 kcal/ml to 15 kcal/ml.

For patients suffering from malabsorption and/or low appetite rather high caloric densities may be preferred. For such patients caloric densities in the range of 7-12 kcal/ml may be used.

The composition may also contain a protein source and/or a carbohydrate source. Easily digestible carbohydrates and/or proteins are preferred.

At least partially hydrolysed proteins are easier to digest and absorb. Hence, it may be desirable to supply at least partially hydrolysed proteins (degree of hydrolysis between 2 and 20%). If hydrolysed proteins are required, the hydrolysis process may be carried out as desired and as is known in the art. For example, a protein hydrolysate may be prepared by enzymatically hydrolysing a protein fraction in one or more steps. For an extensively hydrolysed protein, the proteins may be subjected to triple hydrolysis using Alcalase 2.4 L (EC 940459), then Neutrase 0.5 L (obtainable from Novo Nordisk Ferment AG) and then pancreatin at 55° C.

The amount of fatty acids in the composition of the present invention may be adjusted to the patients needs.

In therapeutic applications, the MAG derivatives are administered in an amount sufficient to at least partially cure or arrest the symptoms of the disease and its complications. An amount adequate to accomplish this is defined as "a therapeutically effective dose". Amounts effective for this purpose will depend on a number of factors known to those of skill in the art such as the severity of the disease and the weight and general state of the patient.

In prophylactic applications, MAG derivatives are administered to a patient susceptible to or otherwise at risk of a particular disease in an amount that is sufficient to at least partially reduce the risk of developing a disease. Such an amount is defined to be "a prophylactic effective dose". Again, the precise amounts depend on a number of patient specific factors such as the patient's state of health and weight.

The compositions of the present invention are to be administered in an amount sufficient to provide the MAG derivatives in a therapeutically effective dose or a prophylactic effective dose.

For example, the composition may comprise the sn-1(3) MAG derivatives in an amount corresponding to about 1% to 40% of the energy of the composition, e.g., of about 5% to 40% of the energy of the composition.

Those skilled in the art will understand that they can freely combine all features of the present invention described herein, without departing from the scope of the invention as disclosed. In particular, features described for the uses of the present invention may be applied to the compositions of the present invention and vice versa.

Further advantages and features of the present invention are apparent from the following Examples and Figures.

FIG. 1 shows examples of EPA glycerides used in the present invention: a mixture of sn-1(3)-monoeicosapentaenoylglycerol.

FIG. 2 shows the incorporation of EPA in red blood cells. Treatments: Control rats fed fish oil with or without Orlistat and rats fed with MAGs described in FIG. 1. Values are means±SEM (n=6).

EXAMPLES

The concept was tested in a lipid maldigestion or malabsorption animal model. The maldigestion or malabsorption condition was obtained using Orlistat, a well known pancreatic and gastric lipases inhibitor. Animals were fed during 21 days with long-chain polyunsaturated fatty acid (LC-PUFAs) supplements containing mainly eicosapentaenoic (EPA) acid. Fish oil was used as a source of triacylglycerols and the different EPA glycerides provided in FIG. 1 and purchased from Cognis GmbH, Germany, were evaluated. Orlistat was given at a level sufficient to decrease lipid absorption by 40%. A group receiving fish oil without Orlistat was used as a positive control. At different time intervals (D-3, D7, D14 and D21), fatty acid profile of red blood cell and plasma lipids were performed. At the end of the experiment, fatty acid profiles of different tissues were determined.

The main objective was to follow the level of EPA in red blood cell and plasma lipids. The main comparison evaluated was the difference in EPA level between groups receiving EPA containing MAGs (FIG. 1) in combination with Orlistat and the positive control group (fish oil+Orlistat).

As an example, data obtained for EPA levels in red blood cell lipids at day 7 are reported in FIG. 2. The statistical evaluation revealed that the use of Orlistat decrease EPA incorporation in red blood cells (comparison between the group receiving fish oil in combination or not with Orlistat). This comparison is very important since it corroborates the validity of the model. The level of EPA incorporated in red blood cells in animals receiving the MAGs containing EPA is statistically higher that the fish oil+Orlistat group (all P values lower that 0.05); and further surprisingly, even higher than the fish oil group.

This example clearly demonstrates that in condition of lipid maldigestion or malabsorption, the incorporation of LC-PUFA provided as triacylglycerols is reduced. However, if LC-PUFA are provided as sn-1(3) MAGs—also in combination with sn-2 MAGs, the incorporation in tissue is not altered and even improved, even in conditions of lipid maldigestion or malabsorption.

The invention claimed is:

1. A method for the treatment of inflammatory disorders, the method comprising administering to a subject suffering from a lipid maldigestion or malabsorption condition a composition comprising a sn-1(3)-monoacylglycerol, wherein the acyl group is a fatty acid having anti-inflammatory properties, the fatty acid selected from the group consisting of eicosapentaenoic acid (EPA), docosahexaenoic acid (DHA), α-linolenic acid (ALA), stearidonic acid, γ-linolenic acid (GLA), dihomo-γ-linolenic acid (DGLA), n-3 docosapentanenoic acid (DPA), sciadonic acid, juniperonic acid, and combinations thereof.

2. The method of claim 1, wherein the sn-1(3)-monoacylglycerol is selected from the group consisting of sn-1(3)-monoeicosapentaenoylglycerol, sn-1(3)-mono docosahexaenoylglycerol, sn-1(3)-monooctadecatrienoylglycerol, sn-1(3)-monooctadecatetraenoylglycerol, sn-1(3)-monoeicosatrienoylglycerol, sn-1(3)-mono docosapentaenoylglycerol, sn-1(3)-monosciadonylglycerol, sn-1(3)-monojuniperonylglycerol or combinations thereof.

3. The method claim 1, wherein the sn-1(3)-monoacylglycerol is sn-1(3)monoeicosapentaenoylglycerol.

4. The method of claim 1, wherein no more than 25 weight-% of the total monoacylglycerols are sn-2 monoacylglycerols.

5. The method of claim 1, wherein the composition has a pH of 5-8.

6. The method of claim 1, wherein the composition is to be stored at 8° C. or below.

7. The method of claim 1, wherein the composition comprises a lipase B inhibitor.

8. The method of claim 1, wherein the composition is selected from the group consisting of a food product, an animal food product, a pharmaceutical composition, a nutritional composition, a nutraceutical, a drink, a food additive and a medicament.

9. The method of claim 1, wherein the composition has a caloric density of 0.5 kcal/ml to 15 kcal/ml.

10. The method of claim 1, wherein the sn-1(3)-monoacylglycerol derivative provides about 5% to 40% of the energy of the composition.

11. The method of claim 1, wherein the sn-1(3)-monoacylglycerol derivative provides about 5% to 40% of the energy of the composition.

12. The method of claim 1, wherein the composition contains a combination of different sn-1(3)-monoacylglycerol derivatives.

13. The method of claim 1 for use in the delivery of fatty acids having anti-inflammatory properties.

14. The method of claim 1, wherein the malabsorption condition is due to pancreatic insufficiency, bile salt deficiency, a mucosal disorder and/or a short gut.

15. The method of claim 1, wherein the inflammatory disorder is selected from the group consisting of acute inflammations, chronic inflammations, Crohn's disease, ulcerative colitis, necrotizing enterocolitis, skin inflammation, inflammatory bowel syndrome, liver inflammation, alcoholic cirrhosis, allergy, atopy, bone inflammation, rheumatoid arthritis, systemic lupus, dermato-myositis, thyroiditis, type I diabetes, celiac disease, Biermer's disease, multiple sclerosis, encephalomyelitis, eye inflammation, obesity-associated inflammation, age-related low-grade inflammation, Blau's syndrome, Alzheimer's disease, cardiovascular diseases, atherosclerosis, and metabolic syndrome.

* * * * *